United States Patent [19]

Gould et al.

[11] Patent Number: 4,859,604
[45] Date of Patent: Aug. 22, 1989

[54] COMPOSITION FOR STABILIZATION OF DIAGNOSTIC REAGENTS

[75] Inventors: Martin Gould, Gibbstown; Sudhakar Vulimiri, West Deptford, both of N.J.

[73] Assignee: Ampor, Inc., Bridgeport, N.J.

[21] Appl. No.: 89,840

[22] Filed: Aug. 27, 1987

[51] Int. Cl.$^4$ ............................................. G01N 31/00
[52] U.S. Cl. ........................................ 436/15; 436/18; 436/509; 436/510; 436/511
[58] Field of Search ........................... 436/8–19, 436/513, 518, 519, 520, 521, 527, 531, 826, 509–511; 252/408.1, 380, 397; 422/57, 56; 424/3; 427/2

[56] References Cited

U.S. PATENT DOCUMENTS

| | | | |
|---|---|---|---|
| 3,666,421 | 5/1972 | Price | 422/57 |
| 3,770,383 | 11/1973 | Price | 422/57 |
| 3,920,580 | 11/1975 | Mast | 436/15 |
| 4,121,905 | 10/1978 | Maurukas | 436/15 |
| 4,189,401 | 2/1980 | Louderback | 436/15 |
| 4,379,847 | 4/1983 | Fruitstone et al. | 436/18 |
| 4,578,282 | 3/1986 | Harrison | 422/57 |

*Primary Examiner*—Barry S. Richman
*Assistant Examiner*—T. J. Wallen
*Attorney, Agent, or Firm*—Norman E. Lehrer

[57] ABSTRACT

Disclosed herein is a composition useful for stabilizing diagnostic reagent which functions to react with a specimen to determine the presence or absence of a biological condition comprising about 0.01 to 35 parts by weight protein or peptide and either (A) about 1 to 90 parts by weight of a saccharide polyol selected from the group consisting of corn syrup and dextrose and optionally up to about 25 parts by weight of a pyrrol, or (B) about 1 to 90 parts by weight of a saccharide polyol and about 0.01 to 25 parts by weight of a pyrrol. Also disclosed is a method of stabilizing such diagnostic reagents comprising using the stabilizing composition, and a diagnositc device comprising a non-absorbent base carrying at least one deposition area in which is carried the evaporative residue of such diagnostic reagent and the stabilizing composition.

11 Claims, No Drawings

COMPOSITION FOR STABILIZATION OF DIAGNOSTIC REAGENTS

BACKGROUND OF THE INVENTION

1. FIELD OF THE INVENTION

This invention relates to the stabilization of diagnostic reagents which are used to detect the presence or absence of a biological condition, usually in blood, serum, plasma, urine, saliva, such as pregnancy, syphillis, rheumatoid factor, infectious mononucleosis, serum sickness, Forssman antibodies, and Beta steptococcal infections.

2. DESCRIPTION OF THE PRIOR ART

Prior diagnostic compositions in general use in this field are normally liquid wherein antibodies, antigens, or hormones are bound onto an inert tag latex, isotope, dye, magnetic bead, etc., so that when the biological substance is mixed with the diagnostic composition, a network is formed and clumps, color change, detectable signal, etc., result to indicate the presence or absence of the condition. These devices must either be freeze dried, causing loss in yield and difficulty to process, or maintained in a frozen or refrigerated condition, which is inconvenient to distribute, transport, and store.

A device is described in U.S. Pat. Nos. 4,578,282 and 4,493,821, which contain similar specifications and are divisionals, both to Harrison, wherein a precoated, "dry" slide is provided. A fixative composition for a proteinaceous substance which is reactive in a diagnostic immunological reaction is provided, comprised of certain pecentages of pyrrolid-2-one (referred to herein as 2-pyrrolidinone), polyol, urea, and zinc salt. There are certain disadvantages to the Harrison device which the present invention improves upon. Price, U.S. Pat. Nos. 3,666,421 and 3,770,383 also show diagnostic test slides which contain dried immunochemical reagent which upon being moistened with body fluid to be tested forms a spot of reaction mixture. In each case in the prior art, the stabilizing composition is insufficient for the purposes of the present invention.

SUMMARY OF THE INVENTION

It is an object of the present invention to provide a diagnostic test device which may be stored at room temperature.

It is a further object to provide a diagnostic device which very efficiently and effectively detects the prsence or absence of biological factors in a sample.

It is a further object to provide a room temperature stable diagnostic system which is useful for detecting the presence of rheumatoid factor, syphillis, pregnancy, infectious mononucleosis, and the like.

Another object is to provide a novel stabilizing composition for diagnostic reagents which allows said reagents to be stored and remain stable at higher temperatures than the unstabilized reagent, usually at room temperature. An additional object is to provide an improved method to stabilize diagnostic reagents, especially when dried on a substrate.

These objects, and others which will become apparent from the following description, are achieved by the present invention which comprises in one aspect a composition useful for stabilizing diagnostic reagent which functions to react with a specimen to determine the preesnce or absence of a biological condition comprising about 0.01 to 35 parts by weight protein or peptide and either (A) about 1 to 90 parts by weight of asaccharide polyol selected from the group consisting of corn syrup and dextrose and optionally up to about 25 parts by weight of a pyrrol, or (B) about 1 to 90 parts by weight of a saccharide polyol and about 0.01 to 25 parts by weight of a pyrrol. In another aspect, the invention comprises diagnostic device which is stable att room temperature comprising a non-absorbent base carrying at least one deposition area in which is carried the evaporative residue of a composition comprising a normally unstable antigen or antibody which functions to react with a specimen to determine the presence or absence of a biological condition, and the stabilizing composition.

DETAILED DESCRIPTION OF THE INVENTION AND THE PREFERRED EMBODIMENTS

The diagnostic reagents which are stabilized according to the present invention are well known in the medical laboratory field. They function to react with a specimen to determine the prsence or absence of a biological condition. Such diagnostic reagents are usually unstable antibodies, enzymes, carbohydrates, glycoproteins, and hormones. Diagnostic reagents of these types have a very limited shelf life and must be kept refrigerated or frozen.

Some examples of such reagents are gamma globulin responsive to rheumatoid factor, cellular stroma responsive to infectious mononucleosis, HCG and anti-HCG antiserum responsive to pregnancy, toluidine red unheated serum test antigen responsive to syphillis, and beta hemalitic strep responsive to throat infections.

This invention provides a novel composition which can be mixed or combined with such diagnostic reagents to stabilize them and allow them to be stored for longer periods than heretofore, and at higher temperatures, usually without refrigeration or freezing, and usually in a ratio of about 1 to about 50 parts of stabilizing composition to about 99 to 50 parts diagnostic reagent.

The stabilizing composition comprises about 0.01 to .35 parts by weight protein or peptide and either (A) about 1 to 90 parts by weight of a saccharide polyol selected from the group consisting of corn syrup and dextrose and optionally up to about 25 parts by weight of a pyrrol, or (B) abou 1 to 90 parts by weight of a saccharide polyol and about 0.01 to 25 parts by weight of a pyrrol.

While any pyrrol may be useful, 2-pyrrolidinone has been found to be especially so, and it is therefore most preferred. Other compounds which have carboxyl, amine, and carbamide groups which may be located distally on the backbone of the compound but, depending on the overall conformation of the compound may be brought together in close proximity to act as the pyrrol structure, for example, vinyl pyrrolidinone.

Although other saccharide polyols may be useful when the pyrrol is present, the corn syrup and dextrose saccharide polyols are especially preferred, and at least one of these two species must be used when the pyrrol is not present. Corn syrup is more preferred andn has been found to work optimally.

The protein or peptide is preferably selected from bovine serum albumin, human serum albumin, and egg albumin. Proteins are made up of one or more polypeptide chains, each consisting of many alpha-amino acid residues covalently linked by peptide bonds, of molecular weight of about 5000 to 1 million or more.

The composition useful for stabilizing the diagnostic reagent may further include about 0.01 to 30 parts of a conditioning agent selected from polyvinyl alcohol, polyvinyl alcohol/acetate, polyethylene glycol, hydroxyalkyl cellulose, and polyalkene acrylamides. In many instances, such conditioning agent is greatly preferred. "Gelvatol" brand of polyvinyl alcohol/acetate is an especially preferred conditioning agent.

An especially preferred stabilizing composition comprises corn syrup, 2-pyrrolidinone, bovine serum albumin, and polyvinyl alcohol/acetate.

Although the composition is useful for stabilizing diagnostic reagent in liquid form, it is especially useful for making a diagnostic device which comprises a non-absorbent base carrying at least one deposition area in which is carried the evaporative residue of the normally unstable diagnostic reagent which functions to react with a specimen to determine the presence or absence of a biological condition, and the stabilizing composition.

The evaporative residue is preferably of an aqueous or aqueous-alcohol solution of the diagnostic reagent and the stabilizing composition.

The device generally has a non-absorbent base which is a substrate which has a glass or plastic surface, and said surface is preferably plastic and is most preferably selected from the group consisting of polystyrene, polyacrylate, polymethacrylate, polyethylene, and polyvinyl chloride. The most preferred surface is a colored oro clear coextruded polystyrene card which has flat surfaces surrounded by raised rings which contain the dried, stabilized diagnostic composition.

The stabilizing composition is mixed with the diagnostic reagent of choice, and the unbound water is evaporated off the mixture under reduced humidity conditions, leaving an evaporative residue which is stable. It is believed that the reagent is stabilized by strengthening the internal hydrogen bonding, thereby maintaining the conformation of the molecule. The albumins or other proteins or peptides act as a ballast protein or sacrificial protein, thereby protecting the diagnostic reagent antigen or antibody. The conditioning agent serves to form a protective skin over the evaporative residue and increases the viscosity and elasticity of the evaporative residue.

In certain applications, buffers may be added to the composition to maintain the pH and the overall concentration of the diagnostic reagent of choice. Certain surfactants may also be added, particularly when the biologically active substance is colloidal or has been rendered colloidal by the absorption or binding to an insoluble substrate such as polystyrene beads or other materials. Certain inorganic or organic salts may be added to the stabilizing composition to maintain the chemical integrity of the background matrix of the diagnostic reagent.

The preferred diagnostic device of the invention is used in practice by adding the patient's specimen, e. g., blood, serum, plasma, urine, and saliva which reconstitutes the evaporative residue, and reacts with the reagent to indicate presence or absence of a biological condition.

The following non-limiting examples are presented to illustrate a few embodiments of the invention.

EXAMPLES

EXAMPLE 1

Rheumatoid Factor

The following ingredients are dissolved together to form a stabilizing composition in accordance with the invention, and then added to a suspension of gamma globulin reagent attached to latex particles at a concentration of 70% by weight reagent and 30% by weight stabilizing composition.

| Ingredients | Concentration |
| --- | --- |
| Polyvinyl alcohol/polyvinyl acetate | 2.6 g |
| Ethanol | 33.0 ml |
| 2-pyrrolidinone | 0.66 ml |
| water | 33.0 ml |
| corn syrup (food grade) | 33.0 ml |
| bovine serum albumin | 0.6 g |

EXAMPLE 2

Infectious Mononucleosis

In thi example, cellular stroma is stabilized. The composition is mixed with dyed horse erythrocyte stroma to form a stabilized diagnostic device for the detection of mononucleosis, serum sickness, and Forssman antibodies.

| Ingredients | concentration |
| --- | --- |
| A. Buffer Solution | |
| Sodium phosphate dibasic | 24.80 g |
| Water added to combined volume | 1000.0 ml |
| potassium phosphate monobasic | 27.20 g |
| water added to combined volume | 1000.0 ml |

Mix the above solutions in equal quantities to obtain a pH of 6.8

| egg albumin solution | |
| --- | --- |
| egg albumin | 6.00 g |
| buffer solution | 243.0 ml |
| Pre-stabilizer solution | |
| Egg Albumin Solution | 243.0 ml |
| 2-pyrrolidinone | 5.0 ml |
| lauramide diethylamine | 1.0 ml |
| sodium azide | 1.0 g |
| Final Stabilizer Solution | |
| Pre-Stabilizer Solution | 250.0 ml |
| Corn syrup | 750.0 ml |

The stabilizer is mixed with 10% by weight blue dyed Horse Stroma, and a volume of 30 microliters is dispensed every well, 30 microliters of horse kidney absorbent is dispensed next to he horse stroma in wells used to confirm infectious mononucleosis in conjunction with serum sickness. The stabilizer used for the Horse Kidney absorbent also contains 55 milligrams of Metanil Yellow to make a yellow spot. The three well test configuration of the three reagents will confirm the disease state. The use of only the Horse Stroma and Horse Kidney absorbent in the test configuration will confirm Infectious Mononucleosis in only a majority of the cases.

EXAMPLE 3 - Indirect Pregnancy

The following stabilizer composition is mixed and added at a concentration of 10% to latex coated with HCG and anti-HCG antiserum (antibody) containing 2.5% by weight Bovine Serum albumin. A volume of 30 microliters of both the reagents is added to the wells as separate spots.

| Ingredients | concentration | |
|---|---|---|
| sodium chloride | 4.00 | g |
| ammonium carbonate | 32.00 | g |
| 2-pyrrolidinone | 5.00 | ml |
| water | 495.00 | ml |
| corn syrup | 500.00 | ml |

EXAMPLE 4 - RPR TRUST (SYPHILIS)

The following solutions are made up and the stabilizer is added to choline chloride-metanil yellow solution and final tagged trust antigen at 2 to 25%. The preferred concentration is 10%. The stabilized toluidine unheated serum test (TRUST) antigen is used as part of the diagnostic device for the detection of syphilis.

| Antigen resuspending solution | | |
|---|---|---|
| Phosphate 0.02 M; 0.1% Thimersol | 500.00 | ml |
| Corn syrup | 125.00 | ml |
| EDTA Na 0.25 M | 50.00 | ml |
| Water | 325.00 | ml |
| Final Trust Antigen Tagged | | |
| VDRL precipitated | amt. ppt. | |
| antigen resuspending solution | 869.00 | ml |
| toluidine red 0.25% suspension | 134.40 | ml |
| Trust Stabilizer Solution | | |
| Phosphate Buffer solution | | |
| Sodium phosphate dibasic | 1.40 | g |
| Potassium phosphate monobasic | 1.37 | g |
| Distilled Water | 1000.00 | ml |
| Stabilizer solution | | |
| polyethylene glycol, mw 200 | 1.40 | ml |
| 2-pyrrolidinone | 2.60 | ml |
| EDTA, Na | 2.18 | g |
| lauramide diethylamine (Monomid 1089, 0.5 mg/ml) | 10.00 | microliters |

EXAMPLE 5
BETA STREP

The following stabilizer solution is made up and added to latex coated with antibody against betta strep and negative control latex coated with rabbit gamma globulines at 2 to 30%, prferably 10%

| egg albumin | 6.00 | g |
|---|---|---|
| 2-pyrrolidinone | 5.0 | ml |
| lauramide diethylamine | 1.0 | ml |
| water | 494.0 | ml |
| corn syrup | 500.0 | ml |

A measured volume of the above mixture is placed within the flat ring surface on a polystyrene card and is allowed to dory at room temperature and at a relative humidity of 10%. When the unbound water is removed, the device is sealed in an aluminum foil pouch or foil is sealed over the device. The device is stable at temperatures of from −20° to 50° C. without any loss in biological activity for over a year.

While the invention has been described and exemplified in great detail, various modificattions and improvements should become apparent to those skilled in the art without departing from the spirit and scope of the invention.

We claim:

1. A diagnostic device comprising a non-absorbent base carrying at least one deposition area in which is carried an evaporative residue of a mixture of combination of (a) a normally unstable at room temperature diagnostic reagent which functions to react with a specimen to determine the presence or absence of a biological condition, and (b) a stabilizing composition comprising abou 0.01 to 35 parts by weight of non-diagnostic protein selected from the group consisting of bovine serum albumin, human serum albumin, and egg albumin, and about 1 to 90 parts by weight of a material selected from the group consisting of corn syrup and dextrose.

2. Device of claim 1 wherein said stabilizing composition further includes up to abou 25 parts by weight of pyrrol.

3. Device of claim 2 whereins aid pyrrol is 2-pyrrolidinone.

4. Device of claim 1 wherein said stabilizing composition further includes about 0.01 to 30 parts of a conditioning agent selected from the group consisting of polyvinyl alcohol, polyvinyl alcohol/acetate, polyethylene glycol, hydroxyalkyl cellulose, and polyalkene acrylamides.

5. Device ofo claim 1 wherein said stabilizing composition comprises corn syrup, 2-pyrrlidinone, bovine serum albumin, and polyvinyl alcohol/acetate.

6. Device of claim 1 wherein said evaporative residue is the evaporative residue of an aqueous solution of said diagnostic reagent and said stabilizing composition.

7. Device of claim 6 wherein said evaporative residue is the evaporative residue of an aqueous-alcohol solutionn of said diagnostic reagent and said stabilizing composition.

8. Device of claim 1 wherein said non-absorbent base is a substrate which has a surface selected from the group consisting of glass and plastic.

9. Device of claim 8 wherein said surface is a plastic selected from the group consisting of polystyrene, polyacrylate, polymethacrylate, polyethylene, and polyvinyl chloride.

10. Device of claim 1 wherein said diagnostic reagent is selected from the group consisting of gamma globulin responsive to rheumatoid factor, cellular stroma responsive to infectious mononucleosis, HCG and anti-HCG antiserum responsive to pregnancy, toluidine red unheated serum test antigen responsive to syphilis, and beta hemalitic strep responsive to throat infections.

11. Device of claim 1 wherein said non-diagnostic protein is bovine serum albumin and said material is corn syrup.

* * * * *